(12) United States Patent
Bozzoni et al.

(10) Patent No.: US 7,947,823 B2
(45) Date of Patent: May 24, 2011

(54) SIRNA EXPRESSION SYSTEM

(75) Inventors: Irene Bozzoni, Rome (IT); Michela Alessandra Denti, Rome (IT); Alessandro Rosa, Rome (IT)

(73) Assignee: Universita degli Studi di Roma "La Sapienza" (IT)

( * ) Notice: Subject to any disclaimer, the term of this patent is extended or adjusted under 35 U.S.C. 154(b) by 504 days.

(21) Appl. No.: 10/564,020

(22) PCT Filed: Jul. 9, 2004

(86) PCT No.: PCT/IT2004/000381
§ 371 (c)(1),
(2), (4) Date: Jan. 9, 2006

(87) PCT Pub. No.: WO2005/005634
PCT Pub. Date: Jan. 20, 2005

(65) Prior Publication Data
US 2006/0217327 A1 Sep. 28, 2006

(30) Foreign Application Priority Data
Jul. 9, 2003 (IT) .............................. RM2003A0335

(51) Int. Cl.
*C07H 21/04* (2006.01)
(52) U.S. Cl. ................... 536/24.5; 536/24.31; 536/24.1; 435/6; 435/325; 435/375; 514/44
(58) Field of Classification Search .................... None
See application file for complete search history.

(56) References Cited

U.S. PATENT DOCUMENTS 6,013,447 A * 1/2000 Nilsen et al. ................... 506/10
2004/0001811 A1 * 1/2004 Kreutzer et al. ............ 424/93.21

OTHER PUBLICATIONS

Sui et al. A DNA vector-based RNAi technology to suppress gene expression in mammalian cells. PNAS, 2002, vol. 99, No. 8: 5515-5520.*

Henderson. Formation of the 3' end of U1 snRNA is directed by a conserved sequence located downstream of the coding region. The EMBO Journal, 1985, vol. 4, No. 7: 1837-1985.*
Skuzeski et al. Synthesis of Human U1 RNA. Journal of Biological Chemistry 1984, vol. 259: 8345-8352.*
Elbashir et al. Analysis of gene function in somatic mammalian cells using small interfering RNAs. Methods 2002, vol. 26: 199-213.*
Giering, J. C., et al., "Expression of shRNA from a tissue-specific pol II promoter is an effective and safe RNAi therapeutic", *Mol Ther.*, 16(9), (Sep. 2008), 1630-1636.
Xia, Halbin, et al., "siRNA-mediated gene silencing in vitro and in vivo", *Nature Biotechnology*, vol. 20 (Oct. 2002), 1006-1010.
Denti, M A., et al., "A new vector, based on the PolII promoter for the U1 snRNA gene, for the expression of siRNAs in mammalian cells", *Molecular Therapy, Academic Press*, San Diego, CA, vol. 10, No. 1, Jul. 2004 XP004 660550, 191-199.
Guangchao, Sui , et al., "A DNA vector-based RNAi technology to suppress gene expression in mammalian cells", *Proceedings of the National Academy of Sciences of the United States of America*, vol. 99, No. 8, XP002311179,(Apr. 16, 2002),5515-5520.
Paul, Cynthia P., "Effective Expression of Small Interfering RNA in Human Cells", *Nature Biotechnology*, 29, vol. 20, No. 5, CP001121066,(2002),505-508.
Xia, Haibin, et al., "RNAi suppresses polyglutamine-induced neurodegeneration in a model of spinocerebella ataxia", *Nature Medicine*, vol. 10, No. 8 (XP002311180),(2004),816-820.
Young, DE M., et al., "Characterizatino of Ribozymes Expressed Using U1 and T7 Vectors for the Intracellular Cleavage of ANF MRNA", *Biochemistry, American Chemical Society*, Easton, PA, US, vol. 33, No. 40,(Oct. 11, 1994),12127-12138.

* cited by examiner

*Primary Examiner* — Kimberly Chong
(74) *Attorney, Agent, or Firm* — Schwegman, Lundberg & Woessner P.A.

(57) ABSTRACT

The authors describe an expression system for the correct, stable and effective expression in mammalian cells of a siRNA comprising: a) a polymerase II RNA-dependent promoter derived from the U1 RNA gene; downstream from the sequence b) suitable restriction sites for the cloning of the sequence transcribing the pre-siRNA; downstream from these sites c) sequences derived from the sequences at 3' of the gene for U1 snRNA that are necessary and sufficient for the correct formation of 3' of the presiRNA.

8 Claims, 6 Drawing Sheets

SEQUENCE LISTING

<160> NUMBER OF SEQ ID NOS: 29

<210> SEQ ID NO 1
<211> LENGTH: 11
<212> TYPE: RNA
<213> ORGANISM: Artificial Sequence
<220> FEATURE:
<223> OTHER INFORMATION: A synthetic pre-siRNA 3' terminus

<400> SEQUENCE: 1
uuuauccccu g                                                         11

<210> SEQ ID NO 2

```
<211> LENGTH: 30
<212> TYPE: DNA
<213> ORGANISM: Artificial Sequence
<220> FEATURE:
<223> OTHER INFORMATION: A synthetic linker oligonucletide

<400> SEQUENCE: 2
gatctggtac cctcgaggct agcggatccg                                        30

<210> SEQ ID NO 3
<211> LENGTH: 30
<212> TYPE: DNA
<213> ORGANISM: Artificial Sequence
<220> FEATURE:
<223> OTHER INFORMATION: A synthetic linker oligonucletide

<400> SEQUENCE: 3
ctagcggatc cgctagcctc gagggtacca                                        30

<210> SEQ ID NO 4
<211> LENGTH: 98
<212> TYPE: DNA
<213> ORGANISM: Artificial Sequence
<220> FEATURE:
<223> OTHER INFORMATION: A synthetic oligonucletide

<400> SEQUENCE: 4
gatctcatac agggcaattg gcagatcaag cgtttgtgta gcgcttgatc tgccaattgc        60
cctttatccc ctgactttct ggagtttcaa aagtagac                               98

<210> SEQ ID NO 5
<211> LENGTH: 98
<212> TYPE: DNA
<213> ORGANISM: Artificial Sequence
<220> FEATURE:
<223> OTHER INFORMATION: A synthetic oligonucletide

<400> SEQUENCE: 5
tcgagtctac ttttgaaact ccagaaagtc aggggataaa gggcaattgg cagatcaagc        60
gctacacaaa cgcttgatct gccaattgcc ctgtatga                               98

<210> SEQ ID NO 6
<211> LENGTH: 98
<212> TYPE: DNA
<213> ORGANISM: Artificial Sequence
<220> FEATURE:
<223> OTHER INFORMATION: A synthetic oligonucletide

<400> SEQUENCE: 6
gatctcatac agggcaattg gcagatcaag cgtttgtgta gcgcttgatc tgccaattgc        60
cctttatccc ctgactttct ggagtttcaa aagtagac                               98

<210> SEQ ID NO 7
<211> LENGTH: 98
<212> TYPE: DNA
<213> ORGANISM: Artificial Sequence
<220> FEATURE:
<223> OTHER INFORMATION: A synthetic oligonucletide

<400> SEQUENCE: 7
tcgagtctac ttttgaaact ccagaaagtc aggggataaa gggcaattgg cagatcaagc        60
gctacacaaa cgcttgatct gccaattgcc ctgtatga                               98

<210> SEQ ID NO 8
```

<211> LENGTH: 84
<212> TYPE: DNA
<213> ORGANISM: Artificial Sequence
<220> FEATURE:
<223> OTHER INFORMATION: A synthetic oligonucletide

<400> SEQUENCE: 8
gatctcgggc aattggcaga tcaagcgttt gtgtagcgct tgatctgcca attgcccttta    60 ctttctggag tttcaaaagt agac    84

<210> SEQ ID NO 9
<211> LENGTH: 84
<212> TYPE: DNA
<213> ORGANISM: Artificial Sequence
<220> FEATURE:
<223> OTHER INFORMATION: A synthetic oligonucletide

<400> SEQUENCE: 9
tcgagtctac ttttgaaact ccagaaagta agggcaattg gcagatcaag cgctacacaa    60
acgcttgatc tgccaattgc ccga    84

<210> SEQ ID NO 10
<211> LENGTH: 113
<212> TYPE: DNA
<213> ORGANISM: Artificial Sequence
<220> FEATURE:
<223> OTHER INFORMATION: A synthetic oligonucletide

<400> SEQUENCE: 10
gatctcgggc aattggcaga tcaagcgttt gacttcgcat gaatgagttc attcatgaag    60
cgaaacgctt gatctgccaa ttgcccttac tttctggagt ttcaaaagta gag    113

<210> SEQ ID NO 11
<211> LENGTH: 113
<212> TYPE: DNA
<213> ORGANISM: Artificial Sequence
<220> FEATURE:
<223> OTHER INFORMATION: A synthetic oligonucletide

<400> SEQUENCE: 11
ctagctctac ttttgaaact ccagaaagta agggcaattg gcagatcaag cgtttcgctt    60
catgaatgaa ctcattcatg cgaagtcaaa cgcttgatct gccaattgcc cga    113

<210> SEQ ID NO 12
<211> LENGTH: 84
<212> TYPE: DNA
<213> ORGANISM: Artificial Sequence
<220> FEATURE:
<223> OTHER INFORMATION: A synthetic oligonucleotide

<400> SEQUENCE: 12
gatctcgggc aattgcgaga tcaagcgttt gtgtagcgct tgatctcgca attgcccttta    60 ctttctggag tttcaaaagt agac    84

<210> SEQ ID NO 13
<211> LENGTH: 84
<212> TYPE: DNA
<213> ORGANISM: Artificial Sequence
<220> FEATURE:
<223> OTHER INFORMATION: A synthetic oligonucleotide

<400> SEQUENCE: 13
ctgagtctac ttttgaaact ccagaaagta agggcaattg cgagatcaag cgctacacaa    60
acgcttgatc tcgcaattgc ccga                                              84

<210> SEQ ID NO 14
<211> LENGTH: 20
<212> TYPE: DNA
<213> ORGANISM: Artificial Sequence
<220> FEATURE:
<223> OTHER INFORMATION: A synthetic probe

<400> SEQUENCE: 14
ggcaattggc agatcaagcg                                                   20

<210> SEQ ID NO 15
<211> LENGTH: 20
<212> TYPE: DNA
<213> ORGANISM: Artificial Sequence
<220> FEATURE:
<223> OTHER INFORMATION: A synthetic probe

<400> SEQUENCE: 15
ggcaattgcg agatcaagcg                                                   20

<210> SEQ ID NO 16
<211> LENGTH: 20
<212> TYPE: DNA
<213> ORGANISM: Artificial Sequence
<220> FEATURE:
<223> OTHER INFORMATION: A synthetic probe

<400> SEQUENCE: 16
cgcttgatct gccaattgcc                                                   20

<210> SEQ ID NO 17
<211> LENGTH: 15
<212> TYPE: DNA
<213> ORGANISM: Artificial Sequence
<220> FEATURE:
<223> OTHER INFORMATION: A synthetic box element

<400> SEQUENCE: 17
gtttcaaaag tagac                                                        15

<210> SEQ ID NO 18
<211> LENGTH: 30
<212> TYPE: DNA
<213> ORGANISM: Artificial Sequence
<220> FEATURE:
<223> OTHER INFORMATION: A synthetic terminator element

<400> SEQUENCE: 18
cccctrcttt ctggagtttc aaaagtagac                                        30

<210> SEQ ID NO 19
<211> LENGTH: 399
<212> TYPE: DNA
<213> ORGANISM: Artificial Sequence
<220> FEATURE:
<223> OTHER INFORMATION: A synthetic oligonucleotide

<400> SEQUENCE: 19
ggatccggta aggaccagct tctttgggag agaacagacg caggggcggg agggaaaaag       60
ggagaggcag acgtcacttc cccttggcgg ctctggcagc agattggtcg gttgagtggc      120
agaaaggcag acggggactg ggcaaggcac tgtcggtgac atcacggaca gggcgacttc      180
tatgtagatg aggcagcgca gaggctgctg cttcgccact gctgcttca ccacgaagga      240

```
gttcccgtgc cctgggagcg ggttcaggac cgctgatcgg aagtgagaat cccagctgtg    300
tgtcagggct ggaaagggct cgggagtgcg cggggcaagt gaccgtgtgt gtaaagagtg    360
aggcgtatga ggctgtgtcg gggcagaggc ccaagatct                           399
```

```
<210> SEQ ID NO 20
<211> LENGTH: 108
<212> TYPE: DNA
<213> ORGANISM: Artificial Sequence
<220> FEATURE:
<223> OTHER INFORMATION: A synthetic oligonucleotide

<400> SEQUENCE: 20
gatctcatac agggcaattg gcagatcaag cgttgtgaag ccacagatga acgcttgatc    60
tgccaattgc cctttatccc ctgactttct ggagtttcaa aagtagac                 108
```

```
<210> SEQ ID NO 21
<211> LENGTH: 108
<212> TYPE: DNA
<213> ORGANISM: Artificial Sequence
<220> FEATURE:
<223> OTHER INFORMATION: A synthetic oligonucleotide

<400> SEQUENCE: 21
tcgagtctac ttttgaaact ccagaaagtc aggggataaa gggcaattgg cagatcaagc    60
gttcatctgt ggcttcacaa cgcttgatct gccaattgcc ctgtatga                 108
```

```
<210> SEQ ID NO 22
<211> LENGTH: 84
<212> TYPE: DNA
<213> ORGANISM: Artificial Sequence
<220> FEATURE:
<223> OTHER INFORMATION: A synthetic oligonucleotide

<400> SEQUENCE: 22
gatctcgggc aattggcaga tcaagcgttt gtgtagcgct tgatctgcca attgccctta    60
ctttctggag tttcaaaagt agac                                           84
```

```
<210> SEQ ID NO 23
<211> LENGTH: 84
<212> TYPE: DNA
<213> ORGANISM: Artificial Sequence
<220> FEATURE:
<223> OTHER INFORMATION: A synthetic oligonucleotide

<400> SEQUENCE: 23
tcgagtctac ttttgaaact ccagaaagta agggcaattg gcagatcaag cgctacacaa    60
acgcttgatc tgccaattgc ccga                                           84
```

```
<210> SEQ ID NO 24
<211> LENGTH: 36
<212> TYPE: DNA
<213> ORGANISM: yeast sp.

<400> SEQUENCE: 24
tgacttcgca tgaatgagtt cattcatgaa gcgaaa                              36
```

```
<210> SEQ ID NO 25
<211> LENGTH: 36
<212> TYPE: DNA
<213> ORGANISM: yeast sp.

<400> SEQUENCE: 25
```

```
tttcgcttca tgaatgaact cattcatgcg aagtca                                  36

<210> SEQ ID NO 26
<211> LENGTH: 77
<212> TYPE: RNA
<213> ORGANISM: Artificial Sequence
<220> FEATURE:
<223> OTHER INFORMATION: A synthetic snRNA sequence

<400> SEQUENCE: 26
auacagggca auuggcagau caagcguugu gaagccacag augaacgcuu gaucugccaa        60
uugcccuuua uccccug                                                      77

<210> SEQ ID NO 27
<211> LENGTH: 67
<212> TYPE: RNA
<213> ORGANISM: Artificial Sequence
<220> FEATURE:
<223> OTHER INFORMATION: A synthetic snRNA sequence

<400> SEQUENCE: 27
auacagggca auuggcagau caagcguuug uguagcgcuu gaucugccaa uugcccuuua        60
uccccug                                                                 67

<210> SEQ ID NO 28
<211> LENGTH: 53
<212> TYPE: RNA
<213> ORGANISM: Artificial Sequence
<220> FEATURE:
<223> OTHER INFORMATION: A synthetic snRNA sequence

<400> SEQUENCE: 28
gggcaauugg cagaucaagc guuuguguag cgcuugaucu gccaauugcc cuu              53

<210> SEQ ID NO 29
<211> LENGTH: 82
<212> TYPE: RNA
<213> ORGANISM: Artificial Sequence
<220> FEATURE:
<223> OTHER INFORMATION: A synthetic snRNA sequence

<400> SEQUENCE: 29
gggcaauugg cagaucaagc guuugacuuc gcaugaauga guucauucau gaagcgaaac        60
gcuugaucug ccaauugccc uu                                                82
```

SIRNA EXPRESSION SYSTEM

CROSS-REFERENCES TO RELATED APPLICATIONS

Figure 1:
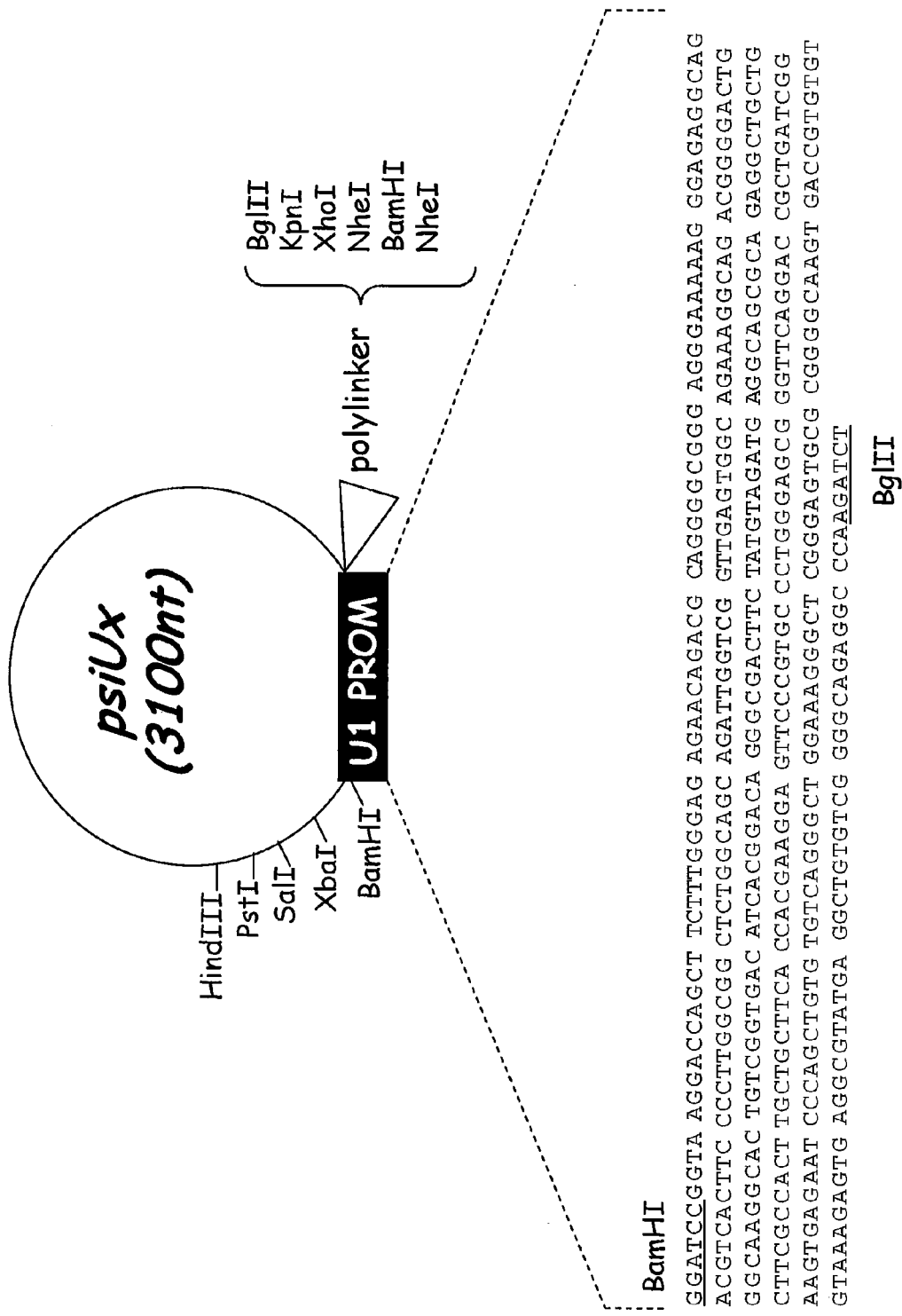

This application is a U.S. National Stage Filing under 35 U.S.C. 371 from International Application Number PCT/IT2004/000381, filed Jul. 9, 2004, and published on Jan. 20, 2005 as WO 2005/0055634 A2, which claimed priority to Application No. RM2003A000335, filed Jul. 9, 2003, which applications and publication are incorporated herein by reference.

The present invention concerns recombinant siRNA vectors based on the regulatory regions of the U1 snRNA gene.

RNA interference is a process of sequence-specific post-transcriptional gene silencing highly conserved in evolution. The mediators of sequence-specific messenger RNA degradation are 21-23 nucleotide small interfering RNAs (siRNAs) generated by ribonuclease III cleavage from longer dsRNAs. Such a process, initially described in *C. elegans* (Fire et al., 1998), and subsequently reported in insects, plants and fungi, has been recently reproduced in mammalian cells through the use of short double-stranded RNAs (21-23 base pairs; Elbashir et al., 2001). Because the efficacy of such molecules is very high, siRNA duplexes may be useful for targeted gene inactivation in human and nonhuman cells and may lead to the development of therapeutics against viral or genetic diseases. Recently, several groups have reported systems designed to introduce siRNAs in mammalian cells through transfection of oligonucleotides (Elbashir et al., 2001; McManus and Sharp, 2002). Since the use of artificial siRNAs has the major drawback of requiring periodic administrations, there is an obvious need to produce plasmids encoding siRNAs in order to obtain a long-term effect.

So far, all siRNA vectors rely on pol III-dependent promoters, such as the U6 snRNA (Lee et al. 2002; Paul et al., 2002) or the H1-RNA (Brummelkamp et al., 2002) genes and more recently a tRNA expressing cassette (Kawasaki and Taira, 2003), patent application WO03/0006477. The authors of the present invention have developed a novel plasmid vector based on the pol II-dependent regulatory regions of the U1 snRNA gene. The U1 promoter is active in all cell types and induces the accumulation of high levels of transcripts. In addition, the presence of a 3' element responsible for the correct 3' end formation of U1 snRNA allows efficient and precise 3' end formation of the transcript.

The constructs of the present invention have the following advantages: i) they have no or very little sequence requirement for 5' and 3' end formation; ii) the pre-siRNA Is rapidly exported to the cytoplasm where it is efficiently converted to the mature form; iii) cloning can be easily performed by means of ds-oligonucleotides, thus avoiding the PCR amplification step which very often produces aberrant products; iv) the U1snRNA gene has a strong pol II promoter which does not undergo silencing in stable cellular clones. Moreover, the authors have identified specific elements that allow the selection of a one single siRNA strand as a response mediator to interference.

Hairpin sequences against the lamin A/C mRNA were inserted between these regulative regions and produced an in vivo efficient accumulation of double-stranded siRNAs of the correct size. Western blot analysis of proteins extracted from HeLa cells transfected with the siRNA expressing plasmids have shown that these vectors, which are the objects of the invention, are very efficient in suppressing the expression of the lamin A/C protein. The sequences that determine an asymmetric release of one of the two double-stranded siRNA have also been identified.

Hence, the object of the present invention is a recombinant vector for the correct, stable and effective expression in mammalian cells of a siRNA or of a miRNA, comprised from 5' to 3':
a) a polymerase II RNA dependent promoter sequence derived from the U1 snRNA gene;
b) suitable restriction sites for cloning the sequence that transcribes a pre-siRNA or a pre-miRNA;
c) a sequence transcribing the pre-siRNA comprising in position +1 an A or a G residue; a sequence from 21 to 23 nucleotides corresponding to a sense region of the mRNA transcribed by the gene to be silenced that constitutes the first segment of the stem of the pre-siRNA; a sequence selected from a pre-miRNA sequence that consists of the loop region of the pre-siRNA; a sequence from 21 to 23 nucleotides corresponding to the antisense region of the mRNA transcribed by the gene to be silenced that constitutes the second segment of the stem of the pre-siRNA; two final residues UU protruding in such a way that the following structure is obtained:

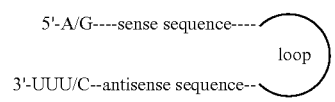

or alternatively a sequence transcribing a pre-miRNA;
d) termination sequences derived from the 3' end sequence of the gene for U1 snRNA which are necessary and sufficient for the correct formation of the 3' end of the pre-siRNA or of the pre-miRNA respectively.

Preferably, the cloning site for thr 5' of the sequence transcribing the pre-siRNA is Bgl II.

Preferably, the sequence transcribing the pre-siRNA further comprises at termini 5' and 3' such sequences that the transcribed pre-siRNA has the following structure:

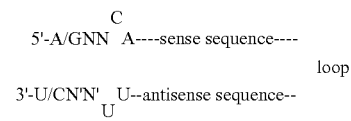

where N is A, U, G or C and N' is its complementary nucleotide.

More preferably, the sequence transcribing the pre-siRNA further comprises at the 5' and 3' termini sequences such that the transcribed pre-siRNA has the following structure:

(SEQ ID NO: 1)

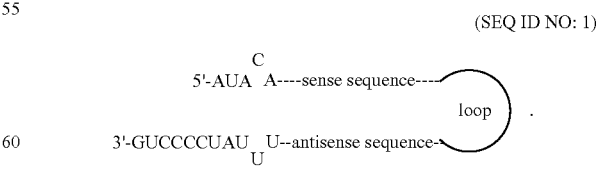

The vectors of the invention are advantageously utilized though they produce lower levels of siRNAs than pol III based vectors. As a matter of fact these levels result to be sufficient to mediate an RNA interference response, with no side effects due to unspecific targeting caused by high transcripts levels.

Then therapeutical applications are safer when the same response is obtained with such lower levels of siRNA. The U1 snRNA gene promoter consists of a Distal Sequence Element (DSE) acting as enhancer of transcription and a Proximal Sequence Element (PSE) that positions transcription initiation. The distance between the PSE and the +1 nucleotide is strictly conserved while its primary sequence is not. This promoter organization is advantageous to modify and convert the same into an inducible promoter.

In the last few years it has been estimated that as many as 1% of human genes encode a group of 20-25 nucleotide long non-coding microRNAs (miRNAs) that play a vital role in the regulation of gene expression in plant and animal species (Bartel, 2004). Their structure and biosynthesis is almost identical to that of siRNAs even though they are transcribed as longer precursors. The vector of the invention is advantageously use also to produce microRNAs.

siRNA Expression Systems Applied to Human Gene Therpy

The use of vectors for the in vivo expression of siRNAs finds very powerful applications as a therapeutic tool to generate RNAi response against selected disease models.

RNAi approaches can be used to knocking down gene expression in order to:
1) down-regulate deleterious gene expression
2) re-activate cellular defenses, and
3) inhibit viral gene expression.

This would enable treatments against many acute and persistent diseases including cancer and other genetic dysfunctions, as well as severe infections.

The effectiveness of the constructs produced against the selected target RNAs can be analyzed:
1) in transfected cells or in established cell lines.
2) in primary cells established from patents and/or in animal models of the specific genetic disease.

Animal models will contribute to the validation of siRNA vectors regarding optimized specificity, potency, stability, and delivery before starting clinical tests in human.

The invention Is described below with examples given in reference to the following figures:

FIG. 1. Schematic representation of the psiUX vector; sites present in the polylinker downstream for the U1 snRNA promoter region are indicated. The sequence of the U1 promoter region extending from position −393 to position −6 with respect to the initiation site is shown below (SEQ IDNO:19).

FIG. 2. Panel A): sequence of different psiUx derivatives and of related oligos. 5'end and 3'end of the transcripts are indicated. Sense and antisense sequences are deduced from the lamin A/C mRNA and are represented by convergent arrows. The mutations introduced in the psiUc$_{mut}$-lam construct are indicated above the sequence. The 3' terminator sequence of the U1 gene is indicated as "3' box". Internal loops and variant sequences present in the psiUb-lam and psiUd-lam constructs are shown in grey. (SEQ ID NOs:20-25) Panel B): Predicted structures of the four tested anti-lamin primary transcripts. The arrows indicate the presumptive sites of processing by the Dicer enzyme. siRNA sequences are shown in bold and italics. Underlined nucleotides identify the sequences derived from the 5' and 3' regions of U1 snRNA. The asterisk represents the monomethyl cap. (SEQ ID NOs: 26-29)

FIG. 3. Analysis of the expression and activity of the siRNAs transcribed by the psiUx-lam constructs. HeLa cells were transfected with 6 µg of the different psiU-lam constructs (lanes psiU) or with 6 µg of U6-lam (lane U6). 2 µg of a control U7 construct were co-transfected in all cases. After 48 hours, total RNA was extracted and 15 µg were analysed by Northern blot on a 10% polyacrylamide-urea gel. Panels A and A'): hybridization with a and a$_{mut}$ probes that recognize the antisense strand (left-pointing arrow). Panel A"): hybridisation with a probe specific for U7 snRNA. The brackets indicate the position of the precursor species. The migration of a pBR322/Mspl molecular size marker is shown on the left. Lane NT contains RNA extracted from untransfected cells. Panel B): hybridization with an a probe that recognizes the sense strand (right-pointing arrow). Panel c): 20 µg of total cellular proteins extracted 70 hours after transfection from the same cells as in the previous experiment were analysed by Western blot analysis with anti-lamin monoclonal antibodies. The arrows point to the two isoforms of lamin (A and C). Below the panel, the Ponceau staining of the filter is shown.

Figure 4:
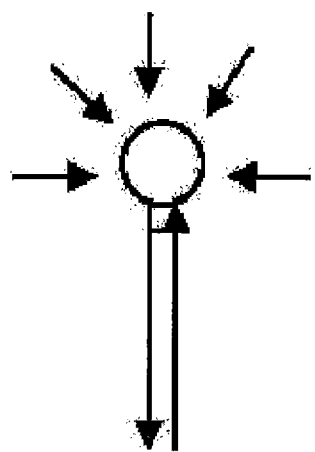
Figure 4:
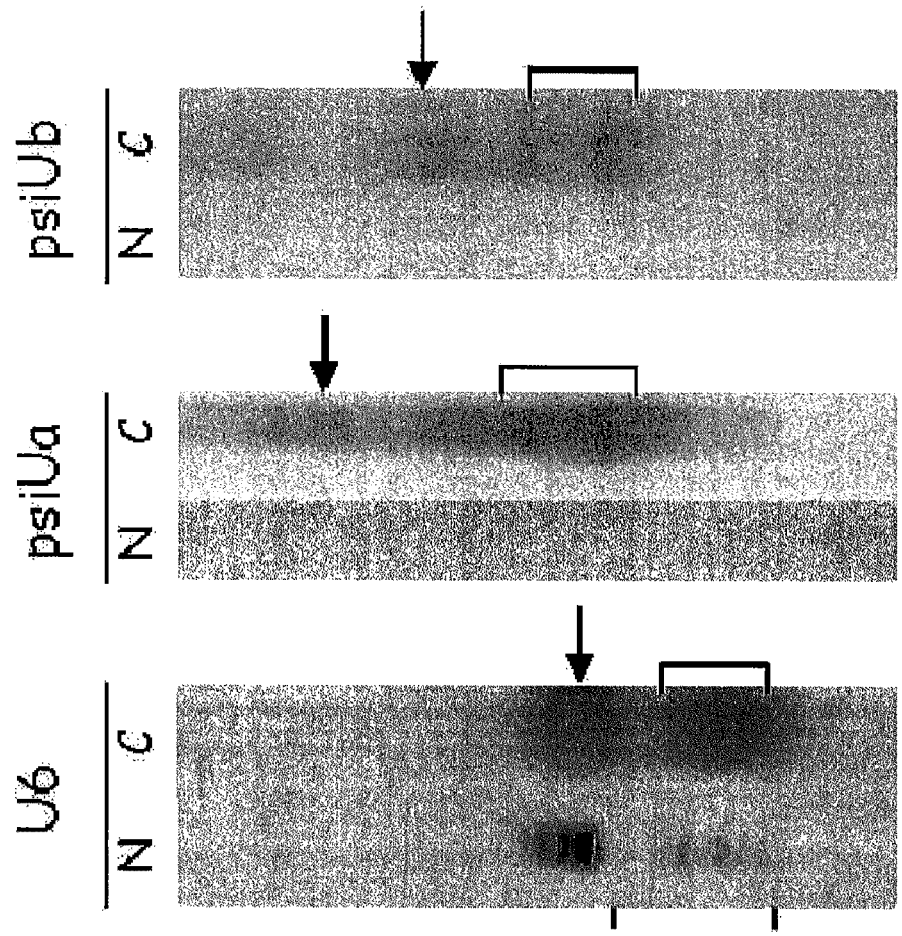

FIG. 4. Analysis of the expression of psiUa-lam, psiUb-lam and U6-lam transcripts in *Xenopus laevis* oocytes. 2.76 ng of plasmid DNA were microinjected into the nucleus of *Xenopus laevis* oocytes. After 12 hours of incubation, RNA was extracted from nuclei (N) and cytoplasms (C) and analysed by Northern blot on a 10% polyacrylamide-urea gel. The arrows indicate the primary transcripts. The brackets indicate the products of cleavage inside the loop (see schematic representation on the side).

MATERIALS AND METHODS

Construction of psiUx vector. The U1 snRNA gene-based vector was derived from plasmid pHU1-ID, containing the entire human gene (De Angelis et al., 2002); this plasmid carries the 600 bp BamHI fragment containing the transcriptional unit of the human U1 snRNA gene inserted in the BamHI site of the pSP65 vector (Promega) in the opposite direction of the SP6 promoter. Plasmid psiUx was derived from the latter by double digestion with BglII and NheI and religation in the presence of a polylinker containing the 5'-BglII, KpnI, XhoI, NheI, BamHI, and NheI-3' sites. The BglII site maps in the U1 snRNA gene, at position −6 with respect to the transcription initiation site, while the NheI site is in the vector, 300 nucleotides upstream from the SP6 promoter. The linker was made by annealing the two oligonucleotides:

```
linkup:   5'-GATCTGGTACCCTCGAGGCTAGCGGATCCG-3'
          (SEQ ID NO: 2)

linkdn:   5'-CTAGCGGATCCGCTAGCCTCGAGGGTACCA-3'
          (SEQ ID NO: 3).
```

Construction of psiU-derivatives expressing siRNAs for the lamin A/C protein.

The selected target sequence on the lamin A/C was derived from Sui et al. (2002) and covers nucleotides 1602-1622 of the X03444 of the NCBI Database. The following oligos: a-lamUP

```
a-lamUP
5'GATCTCATACAGGGCAATTGGCAGATCAAGCGTTGTGAAGCCACAGAT
GAACGCTTGATCTGCCAATTGCCCTTTATCCCCTGACTTTCTGGAGTTTC
AAAAGTAGAC3' (SEQ ID NO: 20)
and a-lamDN
5'TCGAGTCTACTTTTGAAACTCCAGAAAGTCAGGGGATAAAGGGCAATT
GGCAGATCAAGCGTTCATCTGTGGCTTCACAACGCTTGATCTGCCAATTG
CCCTGTATGA3' (SEQ ID NO: 21)
``` were annealed and inserted in the BglII and XhoI sites of psiUx, giving rise to plasmid psiUa- lam. Plasmid psiUb-lam and psiUc-lam were obtained by cloning in the BglII and XhoI sites of psiUx the following oligos:

```
psiUb-lam:
b-lamUP
5'GATCTCATACAGGGCAATTGGCAGATCAAGCGTTTGTGTAGCGCTTGA
TCTGCCAATTGCCCTTTATCCCCTGACTTTCTGGAGTTTCA
AAAGTAGAC3' (SEQ ID NO: 6)
and b-lamDN
5'TCGAGTCTACTTTTGAAACTCCAGAAAGTCAGGGGATAAAGGGCAATT
GGCAGATCAAGCGCTACACAAACGCTTGATCTGCCAATTGC
CCTGTATGA3' (SEQ ID NO: 7)

psiUc-lam:
c-lamUP
5'GATCTCGGGCAATTGGCAGATCAAGCGTTTGTGTAGCGCTTGATCTGC
CAATTGCCCTTACTTTCTGGAGTTTCAAAAGTAGAC3'
(SEQ ID NO: 8)
and c-lamDN
5'TCGAGTCTACTTTTGAAACTCCAGAAAGTAAGGGCAATTGGCAGATCA
AGCGCTACACAAACGCTTGATCTGCCAATTGCCCGA3'
(SEQ ID NO: 9)

psiUd-lam:
d-lamUP
5'GATCTCGGGCAATTGGCAGATCAAGCGTTTGACTTCGCATGAATGAGT
TCATTCATGAAGCGAAACGCTTGATCTGCCAATTGCCCTTACTTTCTGGA
GTTTCAAAAGTAGAG3' (SEQ ID NO: 10)
and d-lamDN
5'CTAGCTCTACTTTTGAAACTCCAGAAAGTAAGGGCAATTGGCAGATCA
AGCGTTTCGCTTCATGAATGAACTCATTCATGCGAAGTCAAACGCTTGAT
CTGCCAATTGCCCGA3' (SEQ ID NO: 11)
```

Plasmid psiUc$_{mut}$-lam was obtained by cloning oligos:

```
cmut-lamUP
5'GATCTCGGGCAATTGcgAGATCAAGCGTTTGTGTAGCGCTTGATCTcg
CAATTGCCCTTACTTTCTGGAGTTTCAAAAGTAGAC3'
(SEQ ID NO: 12) and cmut-lamDN
5'CTGAGTCTACTTTTGAAACTCCAGAAAGTAAGGGCAATTGcgAGATCA
AGCGCTACACAAACGCTTGATCTcgCAATTGCCCGA3'
(SEQ ID NO: 13)
```

(lower case letters indicate nucleotides mutated with respect to the lamin sequence).

Cell Culture And Transfection. Subconfluent HeLa Cells Were Transfected in 60 mm plates by using Lipofectamine 2000 (Life Technologies, Gibco BRL) according to the manufacturer's instructions. 6 µg of psiUx plasmid derivatives were transfected together with 2 µg of plasmid U7-3' (DeAngelis et al., 2002) as an internal control of transfection.

*Xenopus laevis* oocytes microinjections. 9.2 nl of plasmid DNA (300 ng/µ) were injected in the nucleus of stage IV *Xenopus laevis* oocytes according to Caffarelli et aL (1987). After 12 hours of incubation at 19° C., nuclei and cytoplasms were manually dissected and RNA was extracted as described (Caffarelli et al, 1987).

Northern blotting. Total RNA isolation from transiently transfected HeLa cells was done using the Ultraspec RNA isolation system (Biotech Laboratories, Houston) according to the manufacturer's instructions. To detect siRNAs, 15 ug of total RNA were electophoresed in a 10% polyacrylamide-8 M urea gel and transferred by electroblotting onto Hybond-N$^+$ membrane (Amersham Pharmacia Biotech). The hybridisation was carried out at 37° C. in 5X SSPE, 5X Denhardt's solution, 0,5 SDS, 25 ug/ml salmon sperm DNA (Invitrogen). Washes were performed at 37° C. in 6X SSPE and 2X SSPE and 0.2X SSPE. Probes used were terminally $^{32}$P-radiolabelled DNA oligos:

```
probe a:        5'-GGCAATTGGCAGATCAAGCG-3'
                (SEQ ID NO: 14);

probe a-mut:    5'-GGCAATTGcgAGATCAAGCG-3'
                (SEQ ID NO: 15);

α probe:        5'-CGCTTGATCTGCCAATTGCC-3'
                (SEQ ID NO: 16).
```

U7-3' transcript was detected with probe U7a (DeAngelis et aL, 2002).

Immunobloting. Protein extracts (20 µg) were separated on 10% polyacrylamide-SDS gels and transferred to nitrocellulose (ProTran, 10 Schleicher and Schuell). The membranes were blocked with 3% skimmed milk in TBS. Mouse monoclonal anti-lamin A/C antibody (sc-7292, Santa Cruz Biotechnology) diluted 1:200 in TBS/3% skimmed milk was used as primary antibody. The immunostaining was carried out using ECL Western blotting detection system (Amersham UK).

Results

The system takes advantage of the characteristics of the human U1 snRNA gene and of its promoter and terminator regions (Hernandez, 1985; Hernandez and Weiner, 1986). The U1 promoter regulates transcription by RNA polymerase II, is ubiquitously active, and ensures high levels of expression. The primary transcript has a monomethylated cap and the RNA is efficiently exported to the cytoplasm. This is extremely important for efficient processing of the pre-siRNA, since the Dicer enzyme has been shown to localize in the cytoplasm (Billy et al., 2001). In addition the correct 3' end formation of U1 snRNA is directed by a box element (GTTTCAAAAGTAGAC-3'box; SEQ ID NO:17) located 10 nucleotides downstream from the U1 snRNA coding region, which works only in association with the specific U1 promoter sequence (Hernandez and Weiner 1986; de Vegvar et al,. 1986). A similar sequence has been found to direct correct 3' end formation also of the U2 snRNA (Hernandez, 1985). In this respect it has been suggested that these snRNAs must be transcribed by a specialized transcription machinery that differs from that synthesizing mRNAs. Recent work by Medlin et al. (2003) has shown that termination does not occur properly if the CTD of pol II has been deleted, indicating that factors required for 3' end formation are recruited very early during transcription. The region containing the U1 snRNA gene promoter extending from the BamHI site, at position −400, to the BglII site, at position −6 with respect to the initiation site, was cloned into the BamHI/NheI sites of the pSP65 plasmid through the use of a synthetic polylinker (FIG. 1A). The resulting construct (psiUx) has a very strong promoter but lacks the transcription initiation site and the terminator. According to our design, these sequences should be provided by the inserted synthetic double stranded fragment, together with the siRNA target sequences. The initiation sequences is 5'-GATCTCA-3', where the last residue corresponds to the +1 nucleotide of the U1 snRNA (a G is also accepted in this position). The terminator element is 5'-CCCCTG'ACTTTCTGGAGTTTCAAAAGTAGAC-3' (SEQ ID NO:18), where the underlined sequence is the so-called 3' box, located 10 nucleotides downstream from the 3' end of the transcript. The CCCCTG sequence corresponds to the last 6 transcribed nucleotides of the U1 snRNA which have been shown to contribute to an efficient and site-specific 3' end formation (Hernandez, 1985). Cloning of the siRNA precursor sequence into psiUx can be performed very easily by inserting an amplified fragment or annealed synthetic oligonucleotides with ends compatible with the selected sites of the plasmid. While a 5' BglII terminus is obligatory since it is required to restore the initiation site, any of the sites contained in the polylinker (KpnI, XhoI, NheI and BamHI) can be utilized at the 3' end (FIG. 1).

Figure 2A:
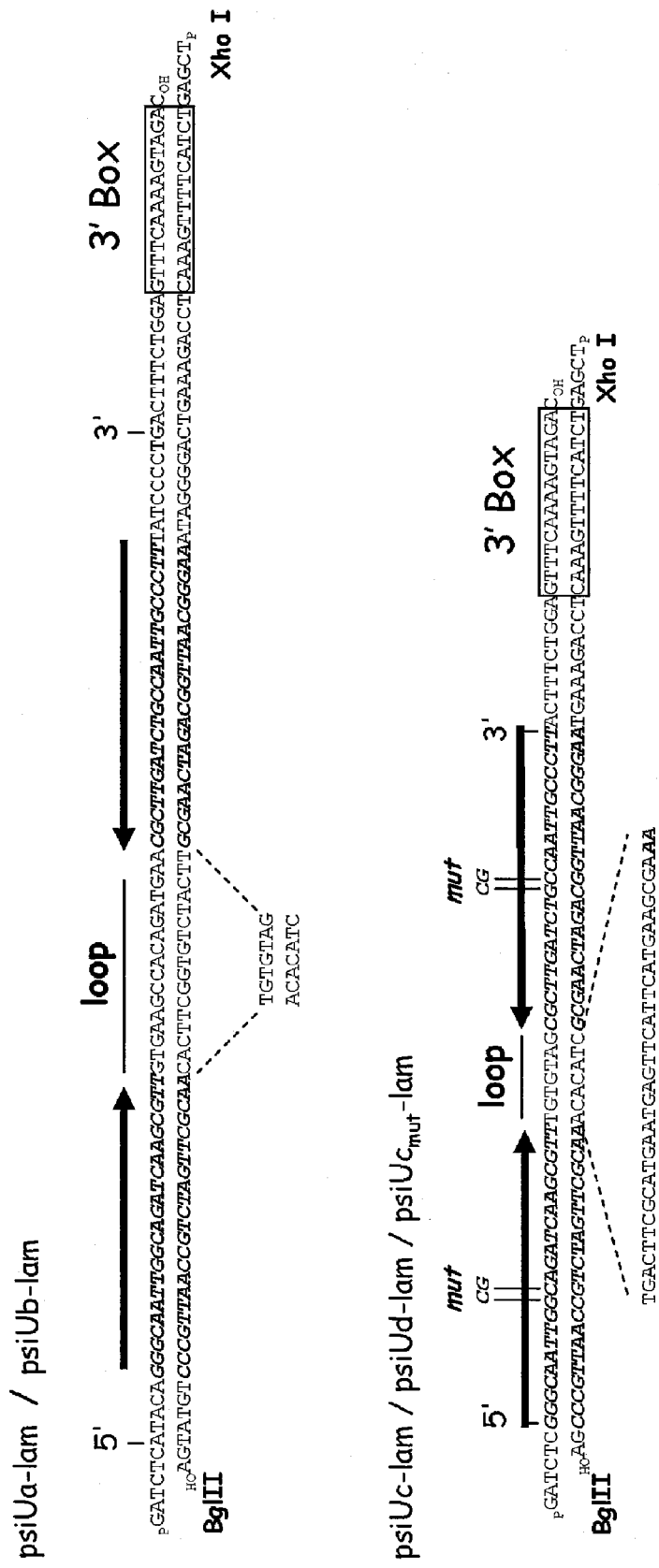
Figure 2B:
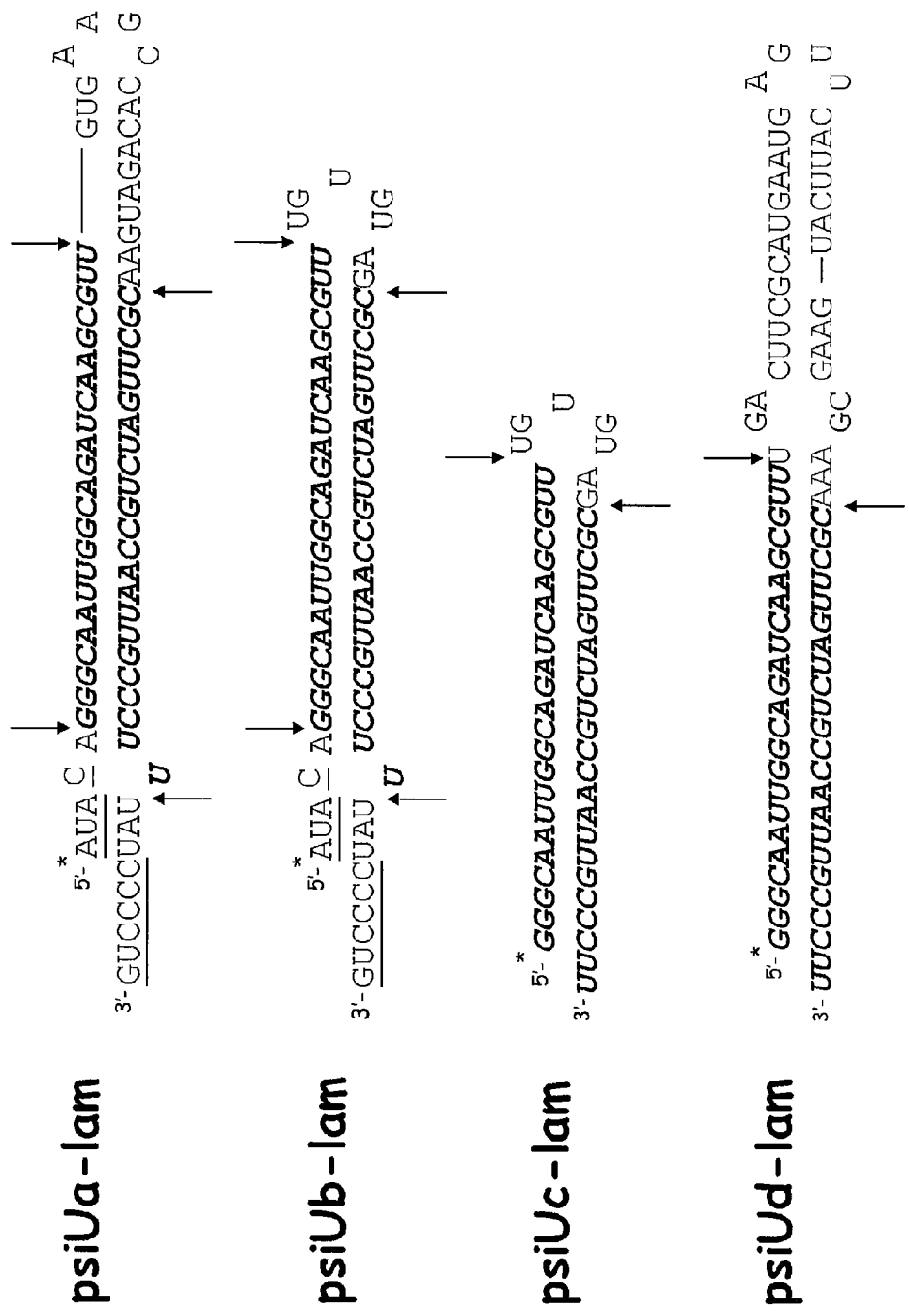

For a target sequence to test the effectiveness of our vector we selected a site in the lamin A/C mRNA demonstrated to be vulnerable to siRNAs (Sui et al., 2002). A hairpin (21 nucleotides sense and antisense sequences derived from the lamin A/C mRNA) was cloned in different contexts In order to identify the most appropriate for efficient siRNA expression (psiU-lam constructs). The resulting constructs differ not only in the type of loop sequence inserted but also in the 5' and 3' ends of the transcribed region. The sequence of the different inserted fragments is indicated in FIG. 2A, and the structure of the primary transcripts is schematically represented in panel B. The loops utilized in psiUa- lam, psiUb-lam and psiUc-lam are deduced from micro pre-RNAs (Zeng et al., 2002 and Castanotto et al., 2002), while that present in psiUd-lam is deduced from the canonical substrate of the yeast Rntl p endonuclease, a RNaseIII-like enzyme (Chanfreau et al., 1998). In addition, constructs psiUa-lam and psiUb-lam contain a terminal region comprising a stem of 3 nucleotides that correspond to the conserved nucleotides at the 5' and 3' ends of the U1 transcript. To prevent Dicer from cleaving in this region, two non-matched bases were inserted. These extensions are absent in psiUc-lam and psiUd-lam. In these constructs, to match the lamin target sequence, the 5' end of the transcript included a G, and the conserved 3' region was converted from CCCCTG to CCCTT.

A control construct was derived with two mismatches of two nucleotides in the central part of the lamin mRNA pairing region from psiUc-lam (psiUcmurlam). This siRNA produced by this construct should be unable to mediate interference response.

To compare the activity of these vector systems with others previously utilized, an anti-lamin A/C hairpin sequence in the U6 vector (plasmid U6-lam) was cloned as described by Sui et al. (2002). The different constructs were tested for expression and activity by transfection into HeLa cells. As an internal control, a modified U7 snRNA gene was co-transfected (DeAngelis et al., 2002) At 48 hours, RNA was extracted and analysed by Northern blot.

Figures 3A, 3B:
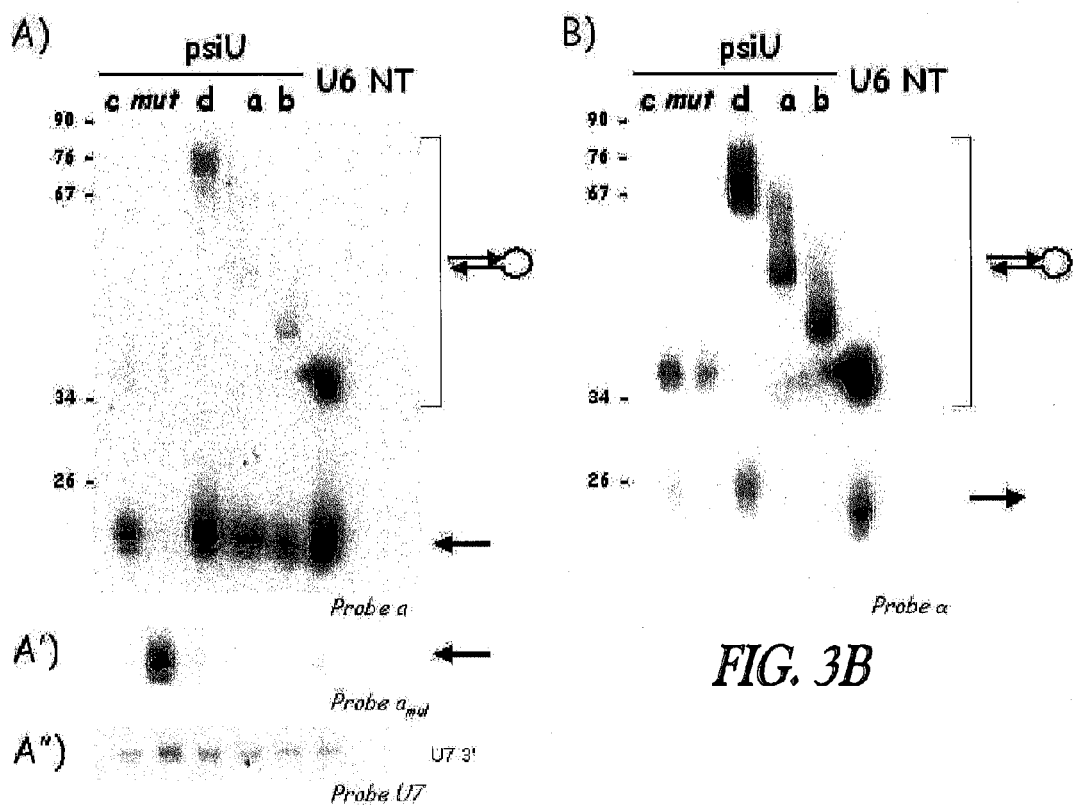
Figure 3C:
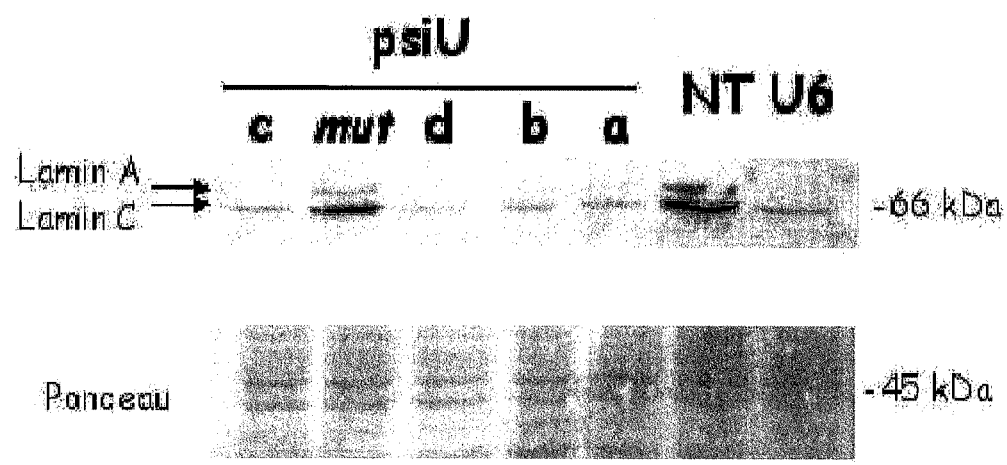

Panels A and A' in FIG. 3 show hybridizations with a specific probe for the sense antisense strand (probe a). All U1-derived constructs produce an accumulation of the antisense strand ranging between 21 and 23 nucleotides. Since these RNAs accumulate in vivo over prolonged times, it can be argued that they are present in stable complexes. Similar findings have been interpreted in other cases as diagnostic for the association with an interference-competent complex. The same type of molecules, in the range of 21-23 nucleotides, accumulates over time in the case of the U6-derived constructs (lane U6). The comparison between the levels of U6 and U1-derived siRNAs, after normalization to the hybridization signal of the co-transfected U7 snRNA (panel A"), indicates that the transcriptional level of psiU-lam constructs is slightly lower than U6-lam. Nevertheless, as shown in FIG. 3C, they mediate the same level of RNA interference response. The sIRNA derived from psiUCmurlam are only visible with the amut probe, which has perfect complementarity to the mutation (FIG. 3A').

The hybridizations performed with the antisense probe (probe a, panel B) reveal an interesting feature: the psiUa-lam and psiUb-lam constructs show no accumulation of the sense strand (the upper strand in FIG. 2B) also when the gel is exposed for lengthy periods. In contrast, all the other constructs showed the production of the sense strand, even if the levels were lower than those of the antisense strands (precursor compared with mature species hybridization signals in panels A and B). These results indicate that the terminal regions of the psiUa-lam and psiUb-lam constructs (FIG. 2B), but not the internal loop, are the element that confers asymmetric selection to the strand included in the interference complex. Expression analysis of the psiU (FIG. 3A) and other independently produced constructs indicate that it is possible to eliminate most of the conserved nucleotides at the 3' end of the U1 snRNA and still obtain efficient termination and processing. Hence, the cloning into the psiUx vector has no sequence constraints, other than the presence of an A or a G at position +1.

An interesting difference between the polIII and polII siRNA vectors is that in the case of U1-driven transcripts only low amounts of precursor (indicated as pre-siRNA) can be detected. On the contrary, this species is much more abundant in the case of the U6 vector (FIG. 3A).

A possible explanation for this difference is that the U6-driven transcripts are not efficiently exported to the cytoplasm. To verify this hypothesis, the U6-lam and psiUa-lam and psiUb-lam plasmids were microinjected into the nucleus of X laevis oocytes, and after 12 hours of incubation RNA was extracted from the nuclear and cytoplasmic compartments. FIG. 4 indicates that a large proportion of the U6-driven transcripts are retained in the nucleus, while no trace of the U1-driven products is found in there. In both cases, only RNA transcripts of the size expected for a precursor molecule are found (pre-siRNA) together with shorter RNA species of the size expected if cleavage had occurred at any position inside the loop region. In the Xenopus system, only tiny amounts of 21-23 nucleotide long species can be visualized after long overexposures, indicating that a Dicer-like activity, if present, is in very low amounts. These data indicate that the pre-siRNAs produced under the U1 promoter are efficiently exported to the cytoplasm.

The same cells analysed for siRNA production were also tested for RNAi activity. 20 micrograms of total protein extracts from cells transiently transfected with U1 and U6-derived constructs were analysed by Western blot analysis with anti lamin A/C antibodies. As shown in FIG. 3B, all siRNA vectors produce good levels of interference if we consider that the efficiency of transfection is in the order of 80-85% (not shown). The level of lamin depletion is similar among all the U1 constructs and to those of the U6-derived expression cassette.

The specificity of the interference response was tested by transfecting into HeLa cells a construct containing two mismatches in the central part of the 21 nucleotide long pairing region (psiUcmurlam). While the accumulation levels of the siRNAs from this construct are similar to those obtained with the parental construct (FIG. 3A') they do not mediate interference as indicated by the levels of lamin accumulation (FIG. 3B, lane mut) that are similar to the control (lane NT).

Altogether, these data indicate that the U1-based vectors have several interesting features compared with other siRNA vectors: i) they have very little sequence requirement at the 5' and 3' termini of the transcripts; ii) they accept U sequences in the transcribed region, unlike what occurs in pol III vectors; iii) cloning is very easy and allows the selection among different cloning sites; iv) primary transcripts are efficiently exported to the cytoplasm and converted to the mature form. In addition, specific sequences can be inserted at the 5' and 3' termini, thus allowing the selection of a single siRNA strand that must be incorporated into the interference complex. This is an important feature for a siRNA vector, in that it eliminates the accumulation of the sense strand that could mediate undesired targeting.

Inducible U1-Based Expression Vector

The U1 snRNA gene promoter consists of a Distal Sequence Element (DSE) acting as enhancer of transcription and a Proximal Sequence Element (PSE) that positions transcription initiation. The distance between the PSE and the +1 nucleotide is strictly conserved while its primary sequence is not. The promoter organization is advantageous to modify and convert the same into an inducible promoter.

One example is represented by the Cre-loxP strategy (Hoess, R. H., A. Wierzbicki, and K. Abremski, 1986; Sauer, B. and N. Henderson, 1988). A long stuffer DNA (containing the information for a selectable marker, i.e. puromycin, neomycin or others), flanked by 2 loxP sites of bacteriophage P1 can be inserted between the PSE and the +1 position. Such insertion prevents transcription of the siRNA. Upon addition of the Cre recombinase the two LoxP sites recombine with the resulting deletion of the stuffer DNA and of one loxP site. Provided that the distance between the PSE and the +1 nucleotide is maintained, the presence of one loxP site does not interfere with promoter activity and transcription of the pre-siRNA occurs.

Expression of MicroRNAs.

miRNA function has been correlated with many complex cellular circuits such as control of cell proliferation, cell death, and fat metabolism in flies, neuronal patterning in nematodes, modulation of hematopoietic lineage differentiation in mammals, and control of leaf and flower development in plants. Recently, a role for microRNAs in oncogenesis has also been proposed. Mainly from studies in worm and flies it has been shown that microRNAs are processed and functionalized in the cell via the RNAi pathway, and that through base pairing to the 3' untranslated region of a mRNA it causes a significant decline in its expression.

The U1-based vector described in this work is utilized also for the production of high levels of miRNAs. In order to optimize miRNA expression two different strategies are followed: 1) the pri-miRNA sequence (this sequence includes a region of approximately 80-110 nucleotides with a well defined secondary structure and can be deduced from genomic data (Griffiths-Jones et al. 2003) is cloned between the promoter and the termination region of the psiUx vector; 2) the miRNA sequence is cloned in psiU as an antisense siRNA sequence.

Altogether, these data indicate that the U1-based vectors have several interesting features compared with other siRNA vectors: i) they have very little sequence requirement at the 5' and 3' termini of the transcripts; ii) they accept U sequences in the transcribed region, unlike what occurs in pol III vectors; iii) cloning is very easy and allows the selection among different cloning sites; iv) primary transcripts are efficiently exported to the cytoplasm and converted to the mature form; v) specific sequences can be added at the 5' and 3' termini, that allow the selection of only one of the two siRNA strands to be incorporated into the interference complex. This is an important feature for a siRNA vector, in that it eliminates the accumulation of the sense strand that could mediate undesired targeting. This is a very crucial aspect that ensures high levels of safety if this expression system has to be used in human clinical protocols.

REFERENCES

Bartel D. P. *Cell.* 2004, 116(2):281-97.
Billy, E., et al. *Proc Natl Acad Sci USA* 25,14428-33 (2001).
Brummelkamp, T. R., Bernards, R. & Agami, R. *Science* 296, 550-553 (2002).
Caffarelli, E., et al. *EMBO J.* 6, 3493-8 (1987).
Castanotto, D., Li, H. & Rossi, J. J. *RNA.* 8,1454-1460 (2002).
Chanfreau, G., Legrain, P. & Jacquier, A. *J. Mol. Biol.* 284, 975-988 (1998).
De Angelis, F. G., et al. *Proc Natl Acad Sci USA.* 99, 9456-9461 (2002).
de Vegvar, H. E., Lund, E. & Dahlberg, J. E. *Cell* 47,259-266 (1986).
Elbashir, S. M., et al. *Nature* 411, 494-498 (2001).
Fire, A., et al. *Nature* 391,806-811 (1998).
Griffiths-Jones S, et al. *Nucleic Acids Res.* 2003 31 (1):439-41.
Hernandez, N. *EMBO J.* 7,1827- 1837 (1985).
Hernandez, N. & Weiner, A. M. *Cell* 47,249-258 (1986).
Hoess, R. H., A. Wierzbicki, and K. Abremski,. *Nucleic Acids Res,* 1986. 14(5): p. 2287-300.
Kawasaki, H. & Taira, K. *Nucleic Acids Res.* 31, 700-707 (2003).
Lee, N. S., et al. *Nat. Biotechnol.* 20,500-505 (2002).
McManus, M. T. & Sharp, P. A. *Nat Rev Genet.* 10,737-747 (2002).
Medlin, J. E., et al. *EMBO J.* 22,925-934 (2003).
Paul, C. P., et al. *Nat. Biotechnol.* 20, 505-508 (2002).
Sauer, B. and N. Henderson. *Proc Natl Acad Sci USA,* 1988. 85(14): p. 5166-70
Sui, G. et al. *Proc Natl Acad Sci USA* 99, 5515-5520 (2002).
Zeng, Y., Wagner, E. J. & Cullen, B. R. *Mol Cell.* 9,1327-1333 (2002).

The invention claimed is:

1. A recombinant vector for the correct, stable and effective expression in mammalian cells of a siRNA or a miRNA, comprising from 5' to 3':

a) an RNA polymerse II dependent promoter sequence derived from the U1 snRNA gene;

b) suitable restriction sites for cloning the sequence that transcribes a presiRNA or a pre-miRNA;

c) a sequence transcribing the pre-siRNA or pre-miRNA comprising: in position +1 an A or a G residue; a sequence from 21 to 23 nucleotides corresponding to a sense region of the mRNA transcribed by the gene to be silenced; a sequence selected to form a loop region; a sequence from 21 to 23 nucleotides corresponding to the antisense region of the mRNA transcribed by the gene to be silenced; wherein the residues at the 3' end protrude in such a way that the following structure is obtained:

5'-YA/G----sense sequence----
                              loop
3'-XUUU/C-antisense sequence-- wherein Y is optionally present, and X and Y if Y is present are independently one or more nucleotides, wherein the nucleotides at the 3' end are selected to result in asymmetry in siRNA or miRNA strand selection into an interference complex; and d) termination sequences derived from the sequence at 3' of the gene for U1 snRNA which are necessary and sufficient for the correct formation of the 3' of the pre-siRNA or of the pre- miRNA, wherein the recombinant vector provides for the correct, stable and effective expression in mammalian cells of a siRNA or a miRNA.

2. The vector according to claim 1, wherein the restriction site for cloning at the 5' end of the sequence transcribing the pre-siRNA is BglII.

3. A recombinant vector for the correct, stable and effective expression in mammalian cells of a siRNA or a miRNA, comprising from 5' to 3':
   a) an RNA polymerse II dependent promoter sequence derived from the U1 snRNA gene;
   b) suitable restriction sites for cloning the sequence that transcribes a presiRNA or a pre- miRNA;
   c) a sequence transcribing the pre-siRNA or the pre-miRNA comprising: in positions +1 an A or a G residue; a sequence from 21 to 23 nucleotides corresponding to a sense region of the mRNA transcribed by the gene to be silenced; a sequence selected to form a loop region; a sequence selected from 21 to 23 nucleotides corresponding to the antisense region of the mRNA transcribed by the gene to be silenced; wherein the residues at the 3' end protrude in such a way that the following structure is obtained:

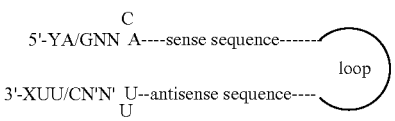

wherein each N is independently A, U, G or C and N' is its complementary nucleotide, wherein Y is optionally present, wherein X and Y if Y is present are independently one or more nucleotides, wherein the nucleotides at the 3' end are selected to result in asymmetry in siRNA or miRNA strand selection into an interference complex; and
   d) termination sequences derived from the sequence at 3' of the gene for U1 snRNA which are necessary and sufficient for the correct formation of the 3' of the pre-siRNA or of the pre-miRNA, wherein the recombinant vector provides for the correct, stable and effective expression in mammalian cells of a siRNA or a miRNA.

4. A recombinant vector for the correct, stable and effective expression in mammalian cells of a siRNA or a miRNA, comprising from 5' to 3':
   a) an RNA polymerse II dependent promoter sequence derived from the U1 snRNA gene;
   b) suitable restriction sites for cloning the sequence that transcribes a presiRNA or a pre- miRNA;
   c) a sequence transcribing the pre-siRNA or the pre-miRNA comprising: in position +1 an A or a G residue; a sequence from 21 to 23 nucleotides corresponding to a sense region of the mRNA transcribed by the gene to be silenced; a sequence selected to form a loop region; a sequence from 21 to 23 nucleotides corresponding to the antisense region of the mRNA transcribed by the gene to be silenced that constitutes the second segment of the stem of the pre-siRNA; wherein the residues at the 3' end protrude in such a way that the following structure is obtained:

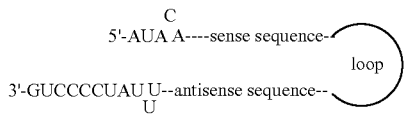

and
   d) termination sequences derived from the sequence at 3' of the gene for U1 snRNA which are necessary and sufficient for the correct formation of the 3' of the pre-siRNA or of the pre-miRNA, wherein the recombinant vector provides for the correct, stable and effective expression in mammalian cells of a siRNA or a miRNA.

5. The vector according to claim 4 wherein the termination sequences derived from the sequence at 3' of the gene for U1 snRNA are as follows:

CCCCTG/ACTTTCTGGAGTTTCAAAAGTAGAC.    (SEQ ID NO:18)

6. The vector according any of claims 1 to 5 further comprising suitable sequences to make inducible the RNA pol II promoter.

7. A recombinant vector for the correct, stable and effective expression in mammalian cells of a siRNA or a miRNA, comprising from 5' to 3':
   a) an RNA polymerse II dependent promoter sequence derived from the U1 snRNA gene;
   b) suitable restriction sites for cloning the sequence that transcribes a presiRNA or a pre- miRNA;
   c) a sequence transcribing the pre-siRNA comprising: in position +1 an A or a G residue; a sequence from 21 to 23 nucleotides corresponding to a sense region of the mRNA transcribed by the gene to be silenced; a sequence selected to form a loop region; a sequence from 21 to 23 nucleotides corresponding to the antisense region of the mRNA transcribed by the gene to be silenced; wherein one of the following structures is obtained:

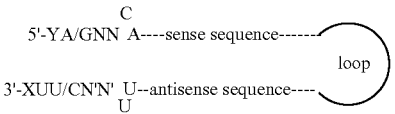

wherein each N is independently A, U, G or C and N' is its complementary nucleotide, wherein Y is optionally present, wherein X and Y if Y is present are independently one or more nucleotides, wherein the nucleotides at the 3' end are selected to result in asymmetry in siRNA strand selection into an interference complex, or

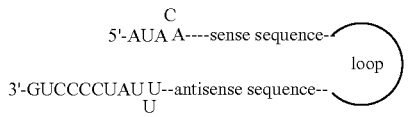

or alternatively a sequence transcribing the pre-miRNA; and
   d) termination sequences derived from the sequence at 3' of the gene for U1 snRNA which are necessary and sufficient for the correct formation of the 3' of the pre-siRNA or of the pre-miRNA.

8. A composition for gene therapy comprising the vector according to claim 1, 3, 4 or 7.

* * * * *

UNITED STATES PATENT AND TRADEMARK OFFICE
CERTIFICATE OF CORRECTION

PATENT NO. : 7,947,823 B2
APPLICATION NO. : 10/564020
DATED : May 24, 2011
INVENTOR(S) : Irene Bozzoni et al.

Page 1 of 3

It is certified that error appears in the above-identified patent and that said Letters Patent is hereby corrected as shown below:

On the face page, in field (56), under "Other Publications", in column 2, line 13, delete "PolII" and insert -- Pol II --, therefor.

On the face page, in field (56), under "Other Publications", in column 2, line 25, delete "spinocerebella" and insert -- spinocerebellar --, therefor.

On the face page, in field (56), under "Other Publications", in column 2, line 27, delete ""Characterizatino" and insert -- "Characterization --, therefor.

In column 1, line 10, delete "2005/0055634" and insert -- 2005/005634 --, therefor.

In column 2, lines 43-47, delete " 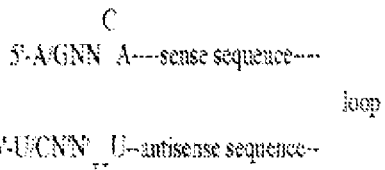 " and insert --  --, therefor.

In column 3, line 41, delete "psiUX" and insert -- psiUx --, therefor.

In column 3, line 42, delete "for" and insert -- from --, therefor.

In column 3, line 45, delete "IDNO:19)." and insert -- ID NO: 19). --, therefor.

Signed and Sealed this
Eleventh Day of October, 2011

David J. Kappos
*Director of the United States Patent and Trademark Office*

CERTIFICATE OF CORRECTION (continued)
U.S. Pat. No. 7,947,823 B2

In column 4, line 67, delete "psiUa- lam." and insert -- psiUa-lam. --, therefor.

In column 5, line 64, delete "electophoresed" and insert -- electrophoresed --, therefor.

In column 6, line 1, delete "0,5" and insert -- 0,5% --, therefor.

In column 6, line 12, delete "α probe:" and insert -- α-probe: --, therefor.

In column 6, line 35, delete "addition" and insert -- addition, --, therefor.

In column 6, line 49, delete "UI" and insert -- U1 --, therefor.

In column 6, line 59, delete "sequences is 5'-GATCTCA-3'," and insert -- sequence is 5'-GATCTC'A-3', --, therefor.

In column 6, line 62, delete "GTTTCAAAAGTAGAC-3'" and insert -- GTTTCAAAAGTAGAC-3' --, therefor.

In column 6, line 66, delete "UI" and insert -- U1 --, therefor.

In column 19, line 54, in Claim 1, delete "polymerse" and insert -- polymerase --, therefor.

In column 20, lines 50-53, in Claim 1, delete "
5'-YA/G----sense sequence----
3'-XUU/C-antisense sequence--- loop
" and insert --
5'-YA/G----sense sequence----
3'-XUU/C-antisense sequence--- loop
--.

In column 20, line 65, in Claim 1, delete "pre- miRNA," and insert -- pre-miRNA, --, therefor.

In column 21, line 3, in Claim 2, delete "BglII ." and insert -- BglII. --, therefor.

In column 21, line 8, in Claim 3, delete "polymerse" and insert -- polymerase --, therefor.

In column 21, line 11, in Claim 3, delete "pre- miRNA;" and insert -- pre-miRNA; --, therefor.

In column 21, line 48, in Claim 4, delete "polymerse" and insert -- polymerase --, therefor.

In column 21, line 51, in Claim 4, delete "pre- miRNA;" and insert -- pre-miRNA; --, therefor.

In column 22, line 5, in Claim 4, after " 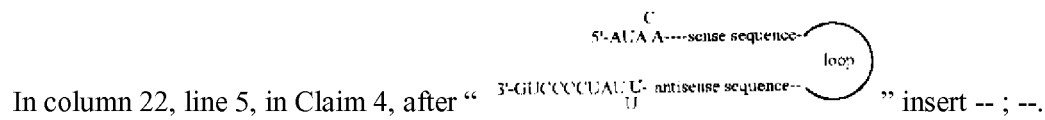 " insert -- ; --.
In column 22, line 28, in Claim 7, delete "polymerse" and insert -- polymerase --, therefor.
In column 22, line 31, in Claim 7, delete "pre- miRNA;" and insert -- pre-miRNA; --, therefor.